United States Patent [19]

Wood et al.

[11] Patent Number: 5,494,799
[45] Date of Patent: * Feb. 27, 1996

[54] IN VITRO ASSAY FOR DETECTING CELL-MEDIATED IMMUNE RESPONSES

[75] Inventors: Paul R. Wood, Lower Templestowe; Leigh A. Corner, Romsey, both of Australia

[73] Assignee: Commonwealth Scientific & Industrial Research Organisation, Campbell, Australia

[*] Notice: The portion of the term of this patent subsequent to Aug. 2, 2011, has been disclaimed.

[21] Appl. No.: 230,373

[22] Filed: Apr. 20, 1994

Related U.S. Application Data

[63] Continuation of Ser. No. 124,439, Sep. 22, 1993, Pat. No. 5,334,504, which is a continuation of Ser. No. 3,662, Jan. 12, 1993, abandoned, which is a continuation of Ser. No. 272,805, Nov. 4, 1988, abandoned.

[30] Foreign Application Priority Data

Mar. 6, 1986 [AU] Australia ............... PH4893
Sep. 6, 1988 [WO] WIPO ............ PCT/AU87/00061

[51] Int. Cl.$^6$ ............ G01N 33/554; G01N 33/569; G01N 33/53; G01N 33/555
[52] U.S. Cl. ........ 435/7.32; 435/7.24; 435/7.9; 435/7.92; 435/863
[58] Field of Search ............ 435/2, 7.24, 7.32, 435/811, 863, 7.9, 7.92; 436/501, 507, 518, 544, 546

[56] References Cited

U.S. PATENT DOCUMENTS

| Number | Date | Inventor | Class |
|---|---|---|---|
| 3,969,497 | 7/1976 | Kniker | 436/543 |
| 4,592,338 | 6/1986 | Blackmore | 436/543 |
| 4,666,865 | 5/1987 | Chang et al. | 436/541 |
| 4,675,282 | 6/1987 | Pang | 435/5 |
| 4,689,397 | 8/1987 | Shinnick et al. | 530/327 |
| 4,708,937 | 11/1987 | Remold | 435/188 |
| 4,745,053 | 5/1988 | Mitsuhashi | 435/5 |
| 5,334,504 | 8/1994 | Wood et al. | 435/7.32 |

FOREIGN PATENT DOCUMENTS

| Number | Date | Country |
|---|---|---|
| 61755/73 | 4/1975 | Australia |
| 1012044 | 6/1977 | Canada |
| 170494 | 2/1986 | European Pat. Off. |
| 2226073 | 12/1974 | France |
| 2353239 | 5/1974 | Germany |
| 49-134398 | 12/1974 | Japan |
| 1443425 | 7/1976 | United Kingdom |

OTHER PUBLICATIONS

Andersson et al.; Scandinavian Journal of Immunology, vol. 20, 425–432, 1984.
Arbeit et al.; Infection and Immunity, vol. 35, No. 2, Feb. 1982, 383–390.
Svedersky et al.; European Journal of Immunology, vol. 12, No. 3, 244–247, 1982.
Journal of Clinical Microbiology, vol. 23, No. 5, May 1986, 911–915.
Kartlunen et al.; Journal of Clinical Microbiology; vol. 22(2), Aug. 1985, 318–319.
Wyatt et al.; Jounral of Immunoogical Methods; vol. 76, 1985, 273–282.
Troyle–Blomberg et al.; Journal of Immunology; vol. 135(5); Nov. 1985; 3498–3504.
Stites et al.; Basic and Clinica Immunlogy, 4th Ed.; 1982; 366–371.
Zinsser Microbiology, 18 ED,; 1984; 410–411 and 560–565.
Aoki et al.; Chemical Abstracts; vol. 95; 1981; Abstract No. 218659e.
Arbeit et al.; Infection and Immunity; vol. 35(7), Feb. 1982; 383–390.
Milner et al.; Res. Vet. Science; 1981; 31; 93–99.
Onwabalili et al.; Clin. Exp. Immunol; 1985; 59; 405–441.
Vilcek et al.; J. Clin. Immunol.; 1986; 6; 146–151.
Nogueira et al.; J. Exp. Med.; 1983; 158; 2165–2170.
Baroja et al.; J. Immunological Methods; 1987; 98; 267–270.
Toossi et al.; J. Exp. Med.; 1986; 163; 1162–1172.
McGraw–Hill Encyclopedia of Science & Technology; 6th Edition, p. 243.
Karttunen et al.; J. Clin. Microbiol; 1987; 25; 1074–1078.
Boom, et al., Infect. Immun., vol. 55, No. 9, pp. 2223–2229, 1987, abstract only.
Andrew, P. W., et al., Eur. J. Immunol., vol. 14, No. 10, pp. 962–964, 1984, abstract only.

Primary Examiner—Toni R. Scheiner
Attorney, Agent, or Firm—Bacon & Thomas

[57] ABSTRACT

An in vitro method and kit for the detection of a cell-mediated immune response to a specific antigen, comprising incubating a whole blood sample with the specific antigen and detecting the presence of gamma interferon released by sensitized lymphocytes in the whole blood sample as an indication of a cell-mediated immune response to the specific antigen.

9 Claims, No Drawings

IN VITRO ASSAY FOR DETECTING CELL-MEDIATED IMMUNE RESPONSES

This application is a continuation of application Ser. No. 08/124,439, filed Sep. 22, 1993; now U.S. Pat. No. 5,334,504 which is a file wrapper continuation of application Ser. No. 08/003,662, filed Jan. 12, 1993, now abandoned, which is a file wrapper continuation of 07/272,805, filed Nov. 4, 1988 now abandoned.

This invention relates to the detection of cell-mediated immune responses, and in particular it relates to an in vitro assay method and kit for the detection of such responses.

It is well-known that when an antigen enters the body, two different types of immune response may occur. The first type, known as the "humoral immune response", involves the synthesis and release of free antibody into the blood and other body fluids; this antibody acting, for example, by coating bacteria to enhance their phagocytosis and by combination with and neutralisation of bacterial toxins. The second type of immune response, known as the "cell-mediated immune response", involves the production of "sensitized" lymphocytes which are themselves the effectors of this type of immunity. This confers protection against organisms such as the tubercle bacillus and viruses which are characterized by an ability to live and replicate within the cells of the host. In individuals immune to tubercle infection, the "sensitized" lymphocytes interact with injected tuberculin antigen to produce the delayed type hypersensitivity skin response which is the basis of the widely-used "Mantoux" skin test in humans.

The present invention relates to the development of a rapid and simple in vitro assay for detecting cell-mediated immune responses in humans and animals. While the invention is particularly described and illustrated herein in relation to the use of the invention in the diagnosis of *Mycobacterium bovis* infection in cattle it will be understood by persons skilled in the art that the assay system is also applicable for use with other animal species as well as humans, and with a wide range of antigens for the diagnosis of other diseases and syndromes. The present invention also has application in the detection of immunity in individuals, as in testing of humans for immunity to tuberculosis as a preliminary step to ascertain whether or not vaccination is required.

The accurate diagnosis of *M.bovis* in cattle is an essential part of the bovine tuberculosis (TB) eradication campaign in Australia. The only test currently in use in the detection of TB in cattle is the tuberculin skin test, which suffers from a number of problems:

1. cattle are required to be held for 3 days to read the test;
2. the sensitivity of the test is poor under certain conditions, e.g. when cattle are heavily stressed; and
3. the injection of tuberculin can interfere with subsequent testing by altering the immunological status of the animals.

Similar problems arise in the use of this test in the detection of TB in man. There has therefore been a long history of attempts to devise alternative tests for the effective diagnosis of TB both in cattle and man. Serological tests have been found to be less satisfactory than the present tuberculin test because of the low levels of antibody generally found in infected animals and the high frequency of non-specific reactions.

The tuberculin reaction is considered to be a classical example of the delayed type hypersensitivity (DTH) response. Over the past 40 years there have been many attempts to find in vitro equivalents of the DTH response. The earliest assay developed and also the most popular has been the lymphocyte proliferation or blast transformation assay (review, Oppenheim and Schecter, 1980). More recently assays based on the release of soluble mediators (lymphokines) by "sensitized" lymphocytes in response to specific antigen have been developed.

All of these in vitro assays have generally required the isolation of lymphocytes from blood, followed by a period of incubation for 2–7 days. The use of whole blood without the requirement for isolation of lymphocytes would provide a simpler, quicker and far more economic assay system.

Whole blood has been used in lymphocyte proliferation assays (Kaneene et al., 1978; Viljanen and Eskola, 1977; Milner et al, 1981), but several technical problems exist:

1. the lymphocyte responses in whole blood cultures generally peak later and require longer incubation periods than assays using isolated lymphocytes;
2. harvesting of these cultures requires repeated washing steps and decolourizing with acetic acid or hydrogen peroxide; and
3. the haemoglobin present quenches the signal when counting the amount of tritiated thyridine incorporated into the DNA of lymphocytes.

An alternative method of assaying would be the measurement of the release of lymphokines in a whole blood culture system, and the measurement of the lymphokine, interleukin-2 (IL-2), in whole blood cultures has been used to detect cell-mediated immunity in humans sensitized against *Francisella tularensis* (Karttunen et al, 1985).

According to the present invention, there is provided an in vitro method of detecting a cell-mediated immune response to a specific antigen in a human or animal, which comprises the steps of:

1. incubating a whole blood sample from the human or animal with the specific antigen; and
2. detecting the presence of gamma interferon ($\gamma$IFN) released by sensitized lymphocytes in said whole blood sample to indicate a cell-mediated immune response to said specific antigen.

In another aspect, this invention also provides a diagnostic kit for the detection of a cell-mediated immune response to a specific antigen in a human or animal, comprising:
   a. a source of the specific antigen;
   b. means for incubating said specific antigen with a whole blood sample from the human or animal; and
   c. means for detecting the presence of gamma interferon ($\gamma$IFN) released by sensitized lymphocytes in the whole blood sample to indicate a cell-mediated immune response to the specific antigen.

The detection of the presence of $\gamma$IFN in the whole blood sample may be performed by any suitable means, for example, by a simple bio-assay as described in detail herein, or by means of an immunoassay such as an enzyme-linked immunoassay (ELISA) using monoclonal antibodies specific for $\gamma$IFN (Le et al, 1984; Tanaka et al, 1985; Van der Meide, 1985). Such detection systems may be simply qualitative, or they may be quantitative of the amount of $\gamma$IFN produced.

According to one specific aspect of this invention, the assay method and kit broadly described above provide a simple and rapid method of detecting the specific cell-mediated immune response to the *M.bovis* antigen, tuberculin purified protein derivative (PPD), in whole blood samples from cattle. The detection of antigen (PPD) specific release of bovine $\gamma$IFN as a measure of cell-mediated immunity (CMI) has been shown to correlate well with the conventional lymphocyte proliferation assay.

The development of a simple whole blood γIFN assay for measuring the responsiveness of cattle to bovine PPD makes this test of practical use in the field for diagnosis of *M.bovis* infections in cattle. In particular, the use of an immunoassay such as ELISA or RIA to quantitate the levels of γIFN produced will provide a simple assay system for use in the field.

The advantages of this system over conventional CMI assays is that it does not require the lengthy separation of lymphocytes or the use of complex tissue culture media. This assay also does not compromise the immune status of the animals as does the current in vivo tuberculin skin test. Furthermore, animals are not required to be held for long periods to read the test results.

In another important aspect, this invention provides a simple and rapid method of testing in vitro for immunity of humans to tuberculosis.

The accuracy of the current tuberculin in vivo skin test for both epidemiological work and as a diagnostic test for tuberculosis in humans has been frequently questioned (Aziz and Haq, 1985; Burstin et. al., 1986). Other workers have also developed in vitro assays that correlated well with the intensity of delayed skin reactivity to purified protein derivative of tuberculin (PPD) in humans (Oppenheim and Schecter, 1980; Geczy and Meyer, 1982). Immunoassays have also been used to quantitate γIFN production as a measure of cellular responsiveness to *M.leprae* and *Plasmodium falciparum* antigens (Kaplan et. al., 1985); Troye-Blomberg et. al. 1985). However all these assays required either the isolation of peripheral blood lymphocytes or lengthy incubation times to obtain satisfactory results, thus making these assays impracticable for general diagnostic purposes.

The ability to use undiluted whole blood samples for the production of gamma interferon in the presence of antigen coupled with the use of a simple immunoassay for detecting the amount of γIFN released, as provided by the present invention, has resulted in the development of a cell-mediated response assay that is far simpler and faster than those previously described.

An additional advantage of an in vitro assay in accordance with this invention over skin testing is that a single blood sample would provide sufficient material for testing a patient's responsiveness to a wide variety of antigens. This would preclude the need for multiple injections and thus avoid the risk of adverse skin reactions e.g vesiculation, ulceration or necrosis may occur at the test site. The injection of antigen into known positive reactors may also result in a febrile reaction or acute hypersensitivity reaction. Multiple skin testing with commonly recognised antigens is used in hospitalised patients to distinguish between antigen specific non-responsiveness and generalised immunosuppression or anergy (Palmer and Reed, 1974; Burstin et. al., 1986).

As previously described, the assay system of this invention is suitable for use in detecting cellular responses to a wide range of other antigens, e.g. *M.leprae, M.tuberculosis,* mumps, Candida, Brucella, histoplasmin, trichophyton, coccidioidin and malaria.

The assay system of the present invention is illustrated by way of example only in the following Examples.

This Example relates to the use of the assay in the diagnosis of *M.bovis* infection in cattle, and compares this method with the conventional lymphocyte proliferation assay.

EXAMPLE 1

I. Materials & Methods

Preparation of peripheral blood lymphocytes (PBL)

Ten to twenty mls of blood is collected into vacutainers containing heparin (20 units/ml) or sodium citrate (3.8%). The blood is then centrifuged at 800 g for 20 min, the buffy coat removed, diluted up to 10 mls with Hanks (GIBCO: $Ca^{++}$, $Mg^{++}$ free) and overlayed onto 10 mls of lymphopaque (BDH: 1.086 g/ml). After centrifuging at 800 g for 25 min the interphase cell layer is collected and washed twice (450 g; 10 min) with 20 mls Hanks. The cells are finally resuspended in 5 ml RPMI 1640 (GIBCO) and viable counts done using eosin (0.2%) exclusion.

Production of Gamma Interferon (γIFN)

(a) Peripheral blood lymphocytes Isolated lymphocytes are cultured ($10^6$ cells/ml) in 1 ml of RPMI 1640 containing 5% foetal calf serum (FCS), L-glutamine (1 mM), 2 mercaptoethanol (2 ME; $5\times10^{-5}$M) and penicillin/streptomycin (100 units/ml). Cells are incubated at 37° C. in 5% $CO_2$ in air for 24–48 hours with antigen (Tuberculin Purified Protein Derivative; PPD) after which their supernatants are harvested and stored at −20° C. prior to assay.

(b) Whole blood cultures Blood samples are collected into vacutainers containing heparin (20 units/ml) and antigen (*M.bovis* PPD 20 μg/ml), and incubated at 37° C. for 24 hours. After centrifuging (450 g, 10 min) the plasma from each tube is removed and stored at −20° C. prior to assay.

Bio-Assay for Bovine Gamma Interferon (γIFN)

$10^4$ bovine kidney cells (MDBK: Flow Labs) are added to each well of a 96 well tray (Nunc) and cultured at 37° C. in 5% $CO_2$ in air for 3 days in RPMI medium containing 10% FCS. When the cell monolayers reach confluency, the medium is removed by suction and replaced with 100 μl of warm RPMI only. 100 μl samples of γIFN supernatants are added to the top wells and serial 2 fold dilutions are prepared down the plate.

After 24 hours the medium is removed and replaced with 100 μl of a 1/500 dilution of stock Semliki forest virus (SFV). After a further 48 hours incubation the cells are fixed with 5% formaldehyde and stained with neutral red (0.02%). The γIFN titer is expressed as the reciprocal of the dilution showing 50% cytopathic effect.

Lymphocyte Proliferation Assay Isolated lymphocytes are cultured in flat-bottom 96 well trays (Nunc) at $2.5\times10^5$ cells/well in RPMI containing 5% FCS, L-glutamine, 2ME and antibiotics. After 48 hour incubation with antigen (25 μl/well) the cultures are pulsed with tritiated thymidine (Amersham; 0.5 μCi/well) and harvested 24 hours later using an automatic cell harvester (Skatron). The amount of tritiated thymidine incorporated is determined using an appropriate scintillant by counting in a liquid β scintillation counter. Results are expressed as mean counts per minute (CPM) of triplicate cultures.

$$\text{Stimulation index } (S.I.) = \frac{\text{mean } CPM \text{ with antigen}}{\text{mean } CPM \text{ without antigen}}$$

Immunization of Cattle

Cattle were immunized by repeated subcutaneous injection of 10 mg of killed *M.Bovis* (AN-5 strain) in 1 ml of saline. Two cows were infected with live *M.Bovis* (AN-5) by either intravenous injection of $10^4$ bacteria or intratracheal injection of $10^7$ bacteria.

II RESULTS

The concentrations of *M.Bovis* antigen (PPD) giving optimal stimulation in the lymphocyte proliferation and γIFN assay were similar (Tables 1 and 2). In a control unimmunized cow PPD even at very high concentrations (50–100 μg/ml), induced very little activity. In the IFN assay the optimal titer of γIFN detected was present by 24 hours using whole blood whereas with isolated peripheral blood lymphocytes higher levels were detected at 48 hours.

When these assay systems were compared with cells from cattle either immunized with killed *M.bovis* or infected with live *M.bovis* there was a good correlation between the results obtained with the two different tests (Tables 3 and 4). Although there were considerable differences in the degree of responsiveness of the different animals all the immunized and infected cattle gave positive responses in the presence of specific antigen.

The cells from *M.bovis* immunized and infected animals also showed little or no response when incubated in the presence of a similar preparation of antigen (PPD) from *Mycobacterium avium,* suggesting that these tests are specific for *M.bovis.*

TABLE 1

Antigen titration in the Lymphocyte Proliferation Assay

| | AN-5 Immunized | | Control | |
|---|---|---|---|---|
| Antigen Conc (μg/ml) | ΔCPM | S.I. | CPM | S.I. |
| Nil | 0 | 1.0 | 0 | 1.0 |
| 1 | 38,321 | 15.5 | 110 | 1.1 |
| 5 | 53,759 | 35.4 | 227 | 1.2 |
| 20 | 63,457 | 41.6 | 1,031 | 1.8 |
| 50 | 63,543 | 41.7 | 1,205 | 2.0 |
| 100 | 68,026 | 44.7 | 1,591 | 2.3 |

ΔCPM = mean CPM with antigen - mean CPM without antigen.

TABLE 2

Antigen titration in γIFN

| | | Conc PPD μg/ml | | | | | |
|---|---|---|---|---|---|---|---|
| | | Nil | 1 | 5 | 20 | 50 | 100 |
| PBL | 24 hr | 0 | 8 | 16 | 32 | 16 | 64 |
| | 48 hr | 2 | 16 | 31 | 64 | 128 | 128 |
| Whole | 24 hr | 0 | 64 | 64 | 128 | 64 | 64 |
| Blood | 48 hr | 0 | 64 | 128 | 128 | 64 | 64 |

Results obtained with whole blood and lymphocytes from an *M. bovis* immunized cow. When cells or whole blood from an un-immunized cow were used γIFN titer were all <2.

TABLE 3

Lymphocyte Proliferation Assay

| | Bovine PPD | | Avian PPD | |
|---|---|---|---|---|
| Immunization | ΔCPM | S.I. | ΔCPM | S.I. |
| Nil | 843 | (1.8) | 418 | (2.0) |
| AN-5 | 47,881 | (33.6) | 2,681 | (2.8) |
| AN-5 | 23,973 | (35.0) | 1,443 | (3.0) |
| AN-5 | 10,327 | (12.3) | 323 | (1.4) |
| Live *M. bovis* | 7,843 | (5.2) | 964 | (1.5) |
| Live *M. bovis* | 40,571 | (14.5) | 1,263 | (1.4) |

TABLE 3-continued

Lymphocyte Proliferation Assay

| | Bovine PPD | | Avian PPD | |
|---|---|---|---|---|
| Immunization | ΔCPM | S.I. | ΔCPM | S.I. |

PPD 20 μg/ml.

TABLE 4

Release of Gamma Interferon

| | | PBL | | | Whole Blood | |
|---|---|---|---|---|---|---|
| Immunization | Nil | Bovine PPD | Avian PPD | Nil | Bovine PPD | Avian PPD |
| Nil | 0 | 0 | 0 | 0 | 0 | 0 |
| AN-5 | 2 | 32 | 4 | 0 | 64 | 0 |
| AN-5 | 2 | 8 | 0 | 0 | 4 | 0 |
| AN-5 | 0 | 8 | 0 | 0 | 16 | 0 |
| Live *M. bovis* | 4 | 64 | 4 | 0 | 64 | 8 |
| Live *M. bovis* | 8 | 64 | 16 | 0 | 256 | 16 |

PPD 20 μg/ml.

EXAMPLE 2

The whole blood IFN assay of this invention as described in Example 1 above was also tested under field conditions for its ability to detect *M. bovis* infected cattle.

Heparinized blood samples were collected from cattle in various herds just prior to tuberculin skin testing these animals. One ml whole blood samples were cultured in the presence of either *M. bovis* PPD, *M. avium* PPD or no antigen and the supernatants collected 24 hours later and assayed for IFN activity.

In herds 1 and 2 the IFN assay of this invention detected 2 *M. bovis* infected animals (Table 5) whereas the skin test detected only one of these animals. The IFN assay was also able to correctly diagnose 4 false positive tuberculin reactors found in herds 3, 4, 5 and 7. It is interesting to note that the four Johnes disease (*Mycobacterium paratuberculosis*) infected animals detected by strong IFN responses to avium/johnin antigen compared to bovis PPD were all sub-clinical cases. Therefore, with the use of an appropriate antigen, the assay of this invention will also be useful for diagnosis of Johnes disease infected cattle.

The test results obtained with the assay of this invention also correlated well with skin testing when used to detect tuberculosis infected water buffalo (Table 6). Six infected animals were positive in both the IFN assay and the skin test and one animal (No. 3) gave a false positive reaction in the skin test. This animal also showed the same degree of IFN activity in both the presence and absence of added antigen which could be due to alpha or beta interferons in the blood sample. The bioassay which was used to detect IFN in this test does not distinguish between the different species of interferons (alpha, beta and gamma). For this reason a positive response in the IFN assay was only recorded when there was an increase in IFN production in the presence of antigen compared to no antigen.

Overall the γIFN test results compared well with the skin test for the diagnosis of tuberculosis. The problem with the presence of other species of interferon in samples from some animals can be resolved by using a monoclonal based immunoassay to quantify the amount of γIFN produced rather than the bioassay used in Examples 1 and 2.

TABLE 5

Field trial of IFN assay for the diagnosis of bovine tuberculosis

| Herd | Size of Herd | #Interferon Titre | | | Skin Test Result | Final Diagnosis |
|---|---|---|---|---|---|---|
| | | Nil | Avium/Johnin | Bovis | | |
| 1 | 90 | 0 | 4 | 64 | + | T |
| 2 | 38 | 0 | 0 | 256 | − | T |
| 3 | NA | 0 | 0 | 0 | + | NVL |
| 4 | NA | 0 | 32 | 8 | ± | J |
| 5 | NA | 0 | 32 | 0 | ± | J |
| 6 | 158 | 2 | 32 | 4 | − | J |
| 7 | 156 | 0 | 16 | 2 | + | J |
| 8 | 4 | 0 | 8 | 8 | + | ST |

The interferon results represent the individual titres of one animal from each of the herds listed. All other animals in these herds were negative in the interferon and skin tests.
NA = not available.
NVL = no visible lesions.
T = Tuberculosis
J = Johnes
ST = Skin Tuberculosis

TABLE 6

Interferon assay trial in a water buffalo herd.

| Animal Number | Interferon Titre | | | Skin Test Result | Final Diagnosis |
|---|---|---|---|---|---|
| | Nil | Avium | Bovis | | |
| 1 | 0 | 0 | 16 | + | T |
| 2 | 0 | 0 | 64 | + | T |
| 3 | 4 | 4 | 4 | + | NVL |
| 4 | 0 | 0 | 64 | + | T |
| 5 | 0 | 0 | 8 | ND | T |
| 6 | 0 | 0 | 128 | + | T |
| 7 | 0 | 0 | 16 | + | T |
| 8 | 2 | 4 | 64 | + | T |

NVL = no visible lesions
ND = not done
T = Tuberculosis

EXAMPLE 3

A trial was established to examine the suitability of the whole blood γIFN assay according to this invention for detection of cellular responses to defined antigens in humans.

Heparinized blood samples were collected from medical students prior to skin testing (Mantoux testing) these individuals. One ml whole blood samples were incubated at 37° C. with *M. bovis* PPD (100 μg/ml) or no added antigen. After 24 hours the supernatants were collected and assayed for γIFN using a monoclonal antibody based radio-immunoassay (Centocor, Pa.). The amount of γIFN present was recorded as counts per minute and converted to γIFN units/ ml by comparison with a standard curve constructed by plotting the γIFN concentration of three known standards versus bound radioactivity. The skin test results were read 72 hours after injection of antigen (10 i.u. PPD; CSL) and recorded as the diameter of the erythema produced. Table 7 shows the skin test result and interferon titres from 34 students.

If a positive response to antigen (PPD) in the interferon assay was recorded for any individual that had an increase of greater than 3 units/ml γIFN in the presence of antigen compared to no antigen, only two results (students 4 and 7) would be at variance with the skin test data. Most of the students were positive in both the skin test and interferon assay, which was expected as the majority of them had been vaccinated against tuberculosis with BCG. Only two individuals (No. 1 and 2) could not recall any previous history of BCG vaccination and both of these students gave negative responses in both assays. A linear regression analysis of this data transformed to log values showed that there was a significant correlation between the two test results (R-square=0.59, P<0.001). Therefore the interferon assay could readily be substituted for the Mantoux test as an assay of cellular reactivity to PPD.

TABLE 7

Gamma Interferon titres and Mantoux skin test diameters for 34 students

| PATIENT | INTERFERON TITRE (UNITS/ML) | | SKIN TEST DIAMETER (mm) |
|---|---|---|---|
| | NO ANTIGEN | PPD | |
| 1 | 0.1 | 0.6 | 0 |
| 2 | 0.8 | 1.0 | 0 |
| 3 | 0.2 | 3.6 | 9 |
| 4 | 0.4 | 4.0 | 0 |
| 5 | 0.6 | 4.0 | 12 |
| 6 | 0.1 | 4.2 | 9 |
| 7 | ND | 6.0 | 0 |
| 8 | 0.1 | 7.0 | 5 |
| 9 | 0.1 | 7.6 | 10 |
| 10 | 0.2 | 8.0 | 9 |
| 11 | 0.4 | 9.0 | 15 |
| 12 | 0.6 | 9.0 | 17 |
| 13 | 0.2 | 9.2 | 10 |
| 14 | 0.2 | 10.0 | 12 |
| 15 | 0.2 | 10.2 | 15 |
| 16 | 0.2 | 12.0 | 12 |
| 17 | 0.1 | 12.4 | 15 |
| 18 | 0.1 | 12.6 | 10 |
| 19 | 0.1 | 13.4 | 9 |
| 20 | 1.0 | 14.6 | 9 |
| 21 | 0.2 | 15.0 | 15 |
| 22 | 2.0 | 16.0 | 25 |
| 23 | 0.6 | 17.2 | 20 |
| 24 | 0.1 | 17.4 | 10 |
| 25 | 0.2 | 17.6 | 10 |
| 26 | 0.7 | 20.0 | 20 |
| 27 | 1.8 | 21.0 | 12 |
| 28 | 0.5 | 21.6 | 25 |
| 29 | 0.2 | 24.0 | 15 |
| 30 | 0.1 | 24.4 | 20 |
| 31 | 0.1 | 26.4 | 20 |
| 32 | 0.1 | 27.8 | 15 |
| 33 | 0.1 | 34.6 | 22 |
| 34 | 0.6 | 36.0 | 16 |

ND = Not done

REFERENCES

1. Aziz, S. and Haq, G. The Mantoux reaction in pulmonary tuberculosis. Tubercle 66, 133–136 (1985).
2. Burstin, S. J., Muspratt, J. A. and Rossing, T. H. The tuberculin test. Studies of the dynamics of reactivity to tuberculin and candida antigen in institutionalized patients. *Am. Rev. Respir. Dis.* 134, 1072–1074 (1986).
3. Geczy, C. L. and Meyer, P. A. Leukocyte procoagulant activity in man: an in vitro correlate of delayed-type hypersensitivity. *J. Immunol.* 128, 331–336, (1982).

4. Kaneene, J. M. B., Johnson, D. W., Anderson, R. K. and Muscoplat, C. C. Comparison of sensitivity and specificity of purified lymphocyte and whole-blood in vitro lymphocyte stimulation assays in detection of *Brucella abortus* infection in cattle. *J. Clin. Micro.* 8, 396–401, (1978).
5. Kaplan, G., Weinstein, D. E., Steinman, R. M., Levis, W. R., Elvers, U., Patarroyo, M. E. and Cohn, Z. A. Analysis of in vitro T cell responsiveness in lepromatous leprosy. *J. Exp. Med.* 162, 917–929, (1985).
6. Karttunen, R., Ilonen, J. and Herva, E. Interleukin 2 production in whole blood culture: a rapid test of immunity to *Francisella tularensis*. *J. Clin. Micro.* 22, 318–319, (1985).
7. Le, J., Barrowclough, B. S. and Vilcek, J. Monoclonal antibodies to human immune interferon and their application for affinity chromatography. *J. Immunol. Methods.* 69, 61–70, (1984).
8. Milner, A. R., Wilks, C. R., and Borland, R. In vitro responses of lymphocytes from cattle and advanced *Mycobacterium paratuberculosis* infection to homologous and heterologous antigens. *Res. Vet. Sc.* 31, 93–99, (1981).
9. Oppenheim, J. J. and Schecter, B. Lymphocyte transformation. In *"Manual of Clinical Immunology"* eds. Rose and Friedman, 233–245, (1980).
10. Palmer, D. L. and Reed, W. P. Delayed hypersensitivity skin testing. I. Response rates in a hospitalized population. *J. Infect. Dis.* 130, 132–137, (1974).
11. Tanaka, E., Imai, M., Sadakazu, U., Tachibana, K., Okamoto, H., Ohike, Y., Nakamura, T., Miyakawa, Y. and Mayami, M. A two-site sandwich radioimmunoassay of human gamma interferon with monoclonal antibodies. *J. Immunol. Methods.* 77, 275–282, (1985).
12. Troye-Blomberg, M., Andersson, G., Stockzkowska, M. Shabo, R., Romero, P., Patarroyo, E., Wigzell, H. and Perlmann, P. Production of IL2 and IFN-γ by T cells from malaria patients in response to *Plasmodium falciparum* or erythrocyte antigens in vitro. *J. Immunol.* 135, 3498–3504, (1985).
13. Van der Meide, P. H., Dubbeld, M. and Schellekens, H. Monoclonal antibodies to human immune interferon and their use in sensitive solid-phase ELISA. *J. Immunol. Methods* 79, 293–305, (1985).
14. Viljanen, M. K. and Eskola, J. PPD-induced lymphocyte transformation in vitro using whole blood. *Clin. Immunol. Immunopathol.* 8, 28–33, (1977).

We claim:

1. A diagnostic kit for the detection of a cell-mediated immune response to a specific antigen in a human or animal, comprising:
   a. a source of the specific antigen;
   b. means for incubating said specific antigen with a whole blood sample from a human or animal; and
   c. means for detecting the presence of gamma interferon (γIFN) released by sensitized lymphocytes in the whole blood sample to indicate a cell-mediated immune response to the specific antigen.

2. A kit according to claim 1, wherein said means for detecting the presence of gamma interferon comprises means for performing an immunoassay for gamma interferon.

3. A kit according to claim 2, wherein said immunoassay means comprises an enzyme-linked immunosorbent assay (ELISA) or a radio-immunoassay (RIA) for gamma interferon.

4. A kit according to claim 1 wherein said specific antigen is an antigen of *Mycobacterium bovis, Mycobacterium paratuberculosis*, or *Mycobacterium tuberculosis*.

5. A kit according to claim 1, for the detection of *M. bovis* infections in cattle, wherein specific antigen is the *M. bovis* antigen, tuberculin purified protein derivative (PPD).

6. A kit according to claim, wherein said specific antigen is an antigen of *Mycobacterium bovis, Mycobacterium paratuberculosis*, or *Mycobacterium tuberculosis*.

7. A kit according to claim 3, wherein said specific antigen is an antigen of *Mycobacterium bovis, Mycobacterium paratuberculosis*, or *Mycobacterium tuberculosis*.

8. A diagnostic kit for the detection of a cell-mediated immune response to a specific antigen in an human or animal which comprises:
   a) a source of specific antigens selected from the group consisting of *Mycobacterium bovis, Mycobacterium paratuberculosis*, and *Mycobacterium tuberculosis*;
   b) means for incubating said specific antigen with a whole blood sample from human or animal; and
   d) means for detecting the presence of a gamma interferon released by sensit lymphocytes in the whole blood sample to indicated a cell-mediated immune response to the specific antigen.

9. A diagnostic kit for the detection of a cell-mediated immune response to a specific antigen in cattle which comprises:
   a) a source of specific antigen which is the *M. bovis* antigen, tuberculin purified protein derivative (PPD);
   b) means for incubating said specific antigen with a whole blood sample from cattle; and
   c) means for detecting the presence of gamma interferon released by sensitized lymphocytes in the whole blood sample to indicate a cell-mediated immune response to the specific antigen.

* * * * *